United States Patent [19]

Ruehl

[11] Patent Number: 5,319,816
[45] Date of Patent: Jun. 14, 1994

[54] IV RACK TRANSFERRABLE FROM AN IV STAND TO A HOSPITAL BED

[75] Inventor: John W. Ruehl, Shelbyville, Ind.

[73] Assignee: Hill-Rom Company, Inc., Batesville, Ind.

[21] Appl. No.: 987,361

[22] Filed: Dec. 7, 1992

[51] Int. Cl.⁵ .......................... A61G 7/00; A61G 7/06
[52] U.S. Cl. ........................................ 5/600; 5/503.1;
5/658; 248/121; 248/223.4; 211/86
[58] Field of Search ............... 248/121, 223.4; 211/74,
211/86; 5/600, 503.1, 658

[56] References Cited

U.S. PATENT DOCUMENTS

| D. 260,816 | 9/1981 | Zissimopoulos et al. |
|---|---|---|
| 1,290,809 | 1/1919 | Truax . |
| 1,490,650 | 4/1924 | Wagner . |
| 2,470,524 | 5/1949 | Scudder . |
| 2,673,771 | 3/1954 | Krewson . |
| 2,696,963 | 12/1954 | Shepherd . |
| 3,337,880 | 8/1967 | Florek ................................. 5/503.1 |
| 3,552,577 | 1/1971 | Latham, Jr. . |
| 3,709,372 | 1/1973 | Alexander ............................ 211/74 |
| 4,225,104 | 9/1980 | Larson . |
| 4,262,872 | 4/1981 | Kodet . |
| 4,511,157 | 4/1985 | Wilt, Jr. . |
| 4,511,158 | 4/1985 | Varga et al. . |
| 4,600,209 | 7/1986 | Kerr, Jr. . |
| 4,725,027 | 2/1988 | Bekanich . |
| 4,729,576 | 3/1988 | Roach . |
| 4,945,592 | 8/1990 | Sims et al. . |
| 4,966,340 | 10/1990 | Hunter . |
| 4,993,683 | 2/1991 | Krauzer . |
| 5,077,843 | 1/1992 | Foster et al. ............................ 5/600 |
| 5,117,521 | 6/1992 | Foster et al. ............................ 5/503.1 X |
| 5,135,191 | 8/1992 | Schmuhl ............................ 5/658 X |

Primary Examiner—Michael F. Trettel
Attorney, Agent, or Firm—Wood, Herron & Evans

[57] ABSTRACT

A wheeled hospital bed, a wheeled IV stand, and an IV rack. The stand and rack include means for removably mounting the rack to the stand, and the stand and bed include means for removably mounting the rack to the bed. When the rack is mounted to the bed the rack and any IV solution bags and pumps mounted thereto are positioned within the bed footprint. The IV stand is universal in that it can be used with or without the severable IV rack.

14 Claims, 3 Drawing Sheets

IV RACK TRANSFERRABLE FROM AN IV STAND TO A HOSPITAL BED

FIELD OF THE INVENTION

This invention relates generally to IV racks, and more particularly to an IV rack which can be used in conjunction with both an IV stand and a hospital bed.

BACKGROUND OF THE INVENTION

The patient critical care environment in hospitals is becoming increasingly crowded due to the number of pieces of medical equipment associated with critical care. Specifically, within the critical care environment, there is generally located a critical care bed, around which are positioned a ventilator, various monitors, one or more computer terminals for entering patient care data and an IV stand which supports one or more bags of IV solution and one or more infusion pumps. The sheer numbers of pieces of equipment spaced about a critical care hospital room and around the patient bed may result in patient care inefficiency, as a care provider must continually monitor and operate all of the pieces of equipment, which pieces of equipment may not be advantageously ergonomically arranged.

In addition to the critical care environment being crowded and somewhat cumbersome around which to work, the transfer of the various pieces of equipment along with the patient on the critical care bed from one room to another within the hospital can be tedious, time consuming and difficult to manage. One reason is that the critical care bed and the various pieces of medical equipment associated with the critical care environment are generally each individually supported on wheeled support structures. Therefore, when transferring the patient from one room to another, several pieces of wheeled equipment typically must simultaneously be rolled to the new location.

One specific piece of equipment which typically must be simultaneously transferred with the critical care bed is a wheeled IV stand, which normally supports a number of bags of IV solution as well as a number of infusion pumps It will be appreciated that simultaneous transfer of the IV stand along with the bed typically is cumbersome and time consuming due to the height of the IV stand, its location of center of gravity, etc.

It has therefore been an objective of the present invention to facilitate the transfer of IV equipment with a hospital bed when transferring the bed from one location to another.

It has been another objective of the present invention to provide for consolidating IV equipment with a hospital bed in order to "clean up" the critical care environment.

SUMMARY OF THE INVENTION

In accordance with the stated objectives and the principles of the present invention, a significant improvement in patient critical care and movement is made by consolidating the patient IV equipment required in a typical critical care environment with the critical care bed for stationary as well as specifically for transportation purposes. That is, rather than rolling the IV stand along with the patient bed from one room to the next, the present invention enables a care provider to roll as a single unit, both the bed and the IV equipment as an integrated critical care unit.

The present invention provides a wheeled IV stand, an IV rack removably secured to the IV stand, and a wheeled hospital bed to which the IV rack is adapted to be removably secured upon transferring the rack from the IV stand to the bed.

More particularly, the hospital bed of the present invention is provided with an IV rail having a pair of vertical posts secured to the bed and a horizontal rail connected between the posts, and a mounting block mounted on the horizontal rail which is slidable along the rail. The mounting block includes a pair of lips on opposed sides which the IV rack is adapted to engage. The mounting block further includes a cam lock whereby the IV rack when mounted thereto may be selectively positioned along the horizontal rail as desired and locked into place.

The IV rack of the present invention is adapted to be secured to the mounting block on the IV rail and comprises a vertical spine, a horizontally oriented arm connected to the spine, and a plurality of individual IV poles connected to the horizontal arm, with the arm and poles adapted to support a plurality of IV bags and infusion pumps. The spine includes on a lower end a dow-turned channel section bracket having inwardly turned flanges which slidably engage the lips on the mounting block on the IV rail.

The present invention also provides a universal IV stand which can either be utilized with the IV rack of the present invention or which can be used as a traditional IV stand. The universal IV stand comprises a wheeled base, a first vertical pole originating at the base and terminating in a platform, a second vertical pole originating at the platform, and a rod slidable upwardly and downwardly into and out of the second vertical pole and including a plurality of hooks at an upper end thereof for supporting bags of IV solution. The platform includes a mounting block thereon which has a pair of lips on opposed sides which the IV rack bracket slidably engages.

Therefore the IV stand with IV rack thereon can be rolled up to a hospital bed adjacent to its IV rail mounting block, and the IV rack can be simply and quickly slidably transferred from the IV stand mounting block to the IV rail mounting block. The bed and IV rack can then be rolled as a single integrated unit. Alternatively, the IV stand can be used without the transferrable IV rack and can simply support bags of IV solution from the vertically adjustable rod as desired.

The typical critical care bed is manufactured to certain external dimensions which, when projected downwardly onto a floor surface, determine the bed's "footprint". The present invention provides for positioning the IV rack on the IV rail such that the IV rack is positioned completely within the bed's footprint such that the outer dimensions of the critical care bed are not exceeded. That is, the present invention advantageously takes advantage of the fact that the bed has been designed to freely travel down aisles, through doors and the like, and of the familiarity of the hospital care provider with maneuvering of the critical care bed.

An advantage of the present invention is that transportation of a critical care bed and IV equipment from one hospital room to another is facilitated.

Another advantage of the present invention is that a universal IV stand is provided which can be employed with an IV rack which is transferrable from the IV stand to a hospital bed, or which can be utilized as a traditional IV stand for supporting bags of IV solution from the stand itself.

Yet another advantage of the present invention is that an IV rack is provided which can be quickly and easily transferred from an IV stand directly to a hospital bed.

Still another advantage of the present invention is that a hospital bed has been provided which incorporates structure for receiving the transfer of an IV rack from an IV stand to the bed for movement of the rack with the bed, yet the rack falls completely within the existing bed footprint when mounted to the bed.

These and other objects and advantages of the present invention will become more readily apparent during the following detailed description taken in conjunction with the drawings herein, in which:

DESCRIPTION OF PREFERRED EMBODIMENTS

Figure 1:
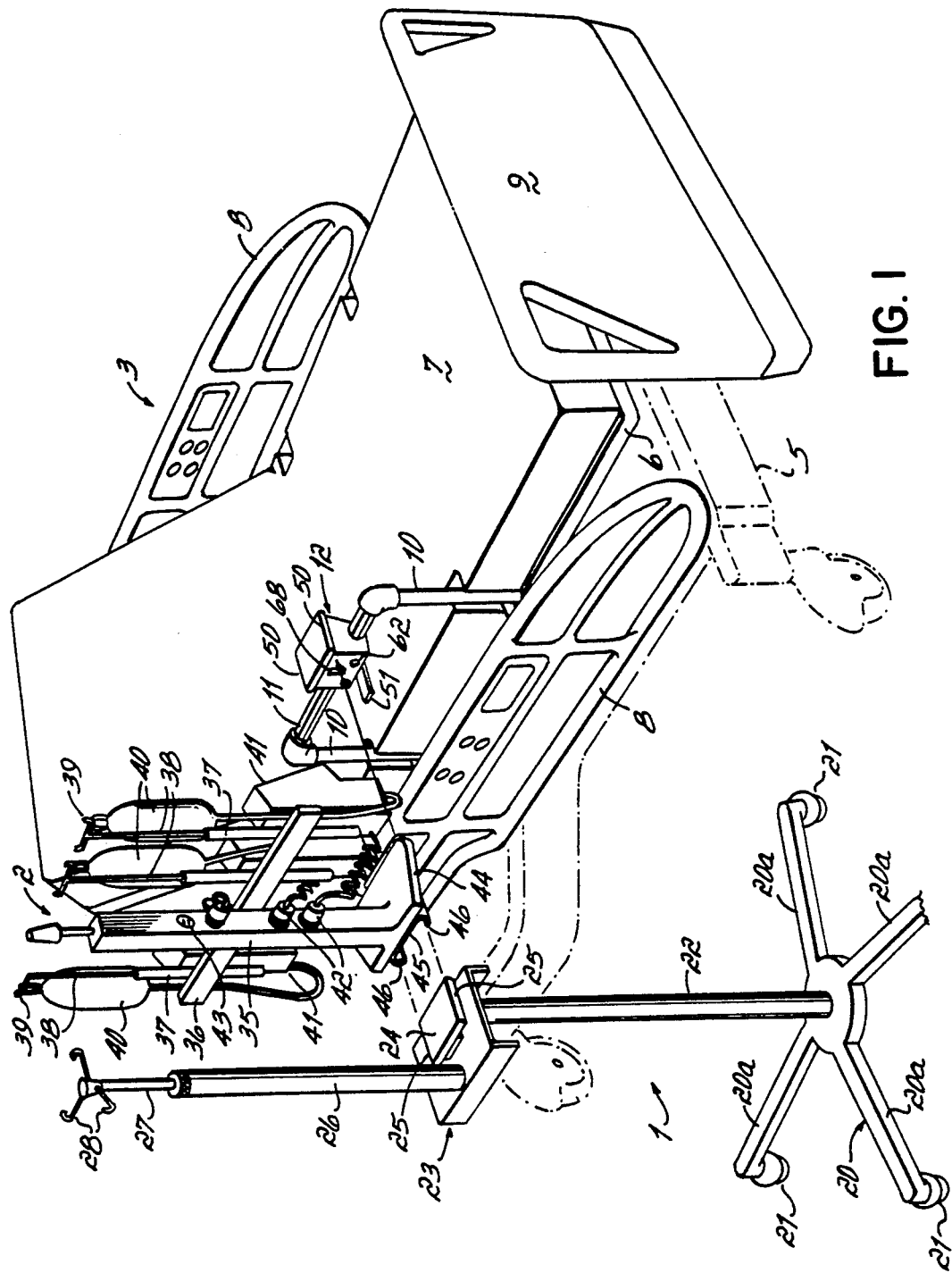
FIG. 1 is a perspective view of the IV rack of the present invention being transferred from the universal IV stand of the present invention to the hospital bed of the present invention.

With reference first to FIG. 1, there is illustrated the IV stand 1, IV rack 2, and hospital bed 3 of the present invention.

The bed 3 includes, generally, a wheeled supporting base structure 5, a patient support 6 mounted atop the wheeled base 5, and a mattress 7 mounted atop the patient support 6. The bed 3 includes a pair of side guards 8,8 which ideally can be raised and lowered. The bed 3 further includes footboard 9. A pair of vertical posts 10,10 are secured to the patient support 6 and extend upwardly therefrom. Spanning between the vertical posts 10,10 is an IV rail 11, being hexagonal in cross section. Mounted to the IV rail 11 is a mounting block 12, the specifics of which will be subsequently described.

The IV stand 1 includes a star shaped base 20, each individual leg 20a of which includes a castered roller 21. Extending upwardly from the base 20 is a first vertical pole 22 which terminates in the platform 23. Platform 23 includes a mounting block 24 thereon, which itself includes a pair of lips 25,25 on opposed sides thereof. A second vertical pole 26 extends upwardly from platform 23, and a rod 27 is adapted for slidable movement upwardly and downwardly into and out of the second vertical pole 26 for telescopic adjustment. The rod 27 includes a number of hooks 28 at its upper end for supporting bags of IV solution thereon.

The IV rack 2 includes a vertical spine 35 to which is attached a horizontally oriented arm 36. Connected to the horizontally oriented arm 36 are a plurality of IV poles 37 each of which includes a telescoping rod 38 outfitted with hooks 39 at their upper ends. Hooks 39 support a plurality of IV solution bags 40, the solution for which is pumped by a number of IV pumps 41 secured to the horizontal arm 36. The IV pumps 41 include plugs 42 which are plugged into sockets 43 in the spine 35 of the IV rack 2, the rack 2 including therein a suitable power supply. The spine 35 includes a base 44 which has mounted thereon a downturned channel section bracket 45 having inwardly turned flanges 46,46 thereon. Inwardly turned flanges 46,46 of bracket 45 slidably mate with the opposed lips 25,25 of the IV stand mounting block 24.

Figure 3:
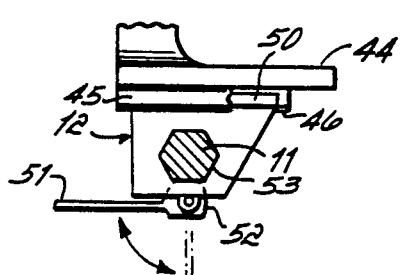
FIG. 3 is a view taken along lines 3—3 of FIG. 2 illustrating the cam lock device of the mounting block.

Mounting block 12 of the hospital bed 3 similarly includes a pair of opposed lips 50,50 for engagement by the inwardly turned flanges 46,46 of the downturned channel section 45 of the IV stand 2. The block 12 further includes a lock lever 51 which rotates a cam 52 for locking the block 12 at any desired longitudinal position along the rail 11 (FIG. 3). The block 12 includes a hexagonal hole 53 which accepts and is adapted for sliding along the rail 11 and for preventing the block 12 from rotating in either lateral direction when the IV rack 2 is mounted thereon.

Figure 4:
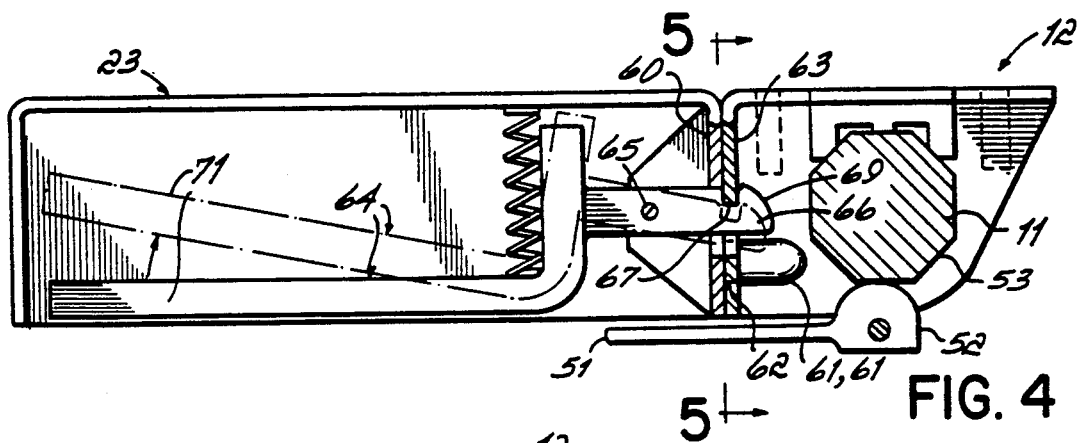
FIG. 4 is a partial side elevational view illustrating the IV stand mated with the IV rail mounting block.
Figure 5:
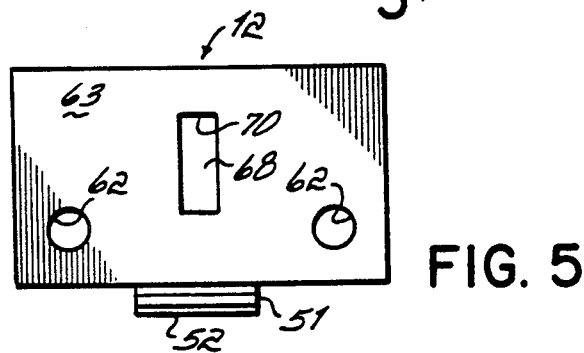
FIG. 5 is a view taken along lines 5—5 of FIG. 4.

When the IV rack 2 is mounted on the IV stand 1, and to transfer the rack 2 from the stand 1 to the bed 3, the stand 1 is rolled up to the bed 3 adjacent its IV rail 11. Referring now to FIG. 4, the bed-facing vertically oriented flange 60 of platform 23 is advanced toward the mounting block 12, and a pair of pins 61,61 mounted on this flange 60 pick up a pair of holes 62,62 in the IV stand-facing vertically oriented flange 63 of the block 12. Mounted underneath the platform 23 is a spring loaded lever 64 which is pivoted at 65, which includes a forwardly projecting tang 66 which has a notch 67 on its upper edge. Tang 66 projects through an aperature (not shown) in flange 60. The vertically oriented flange 63 of block 12 further includes a rectangular cut-out 68 for receiving tang 66 of lever 64. As pins 61,61 enter the alignment holes 62,62 tang 66 is centered with respect to rectangular cut-out 68; the rounded surface 69 of tang 66 rides downwardly against the upper surface 70 of cut-out 68 until such time as notch 67 is directly underneath of upper surface 70, at which time the tang 66 snaps upwardly, thereby locking notch 67 and hence lever 64 to cut-out 68.

With the stand 1 thus secured to the bed 3, the IV rack 2 may then be simply slid from the IV stand mounting block 24 to the IV rail mounting block 12. After the rack has been transferred from the stand 1 to the IV rail 11, handle 71 of lever 64 is raised upwardly thereby allowing the notch 67 of tang 66 to clear upper surface 70 of aperture 68, at which time the IV stand 1 can be rolled away from the bed 3.

Figure 2:
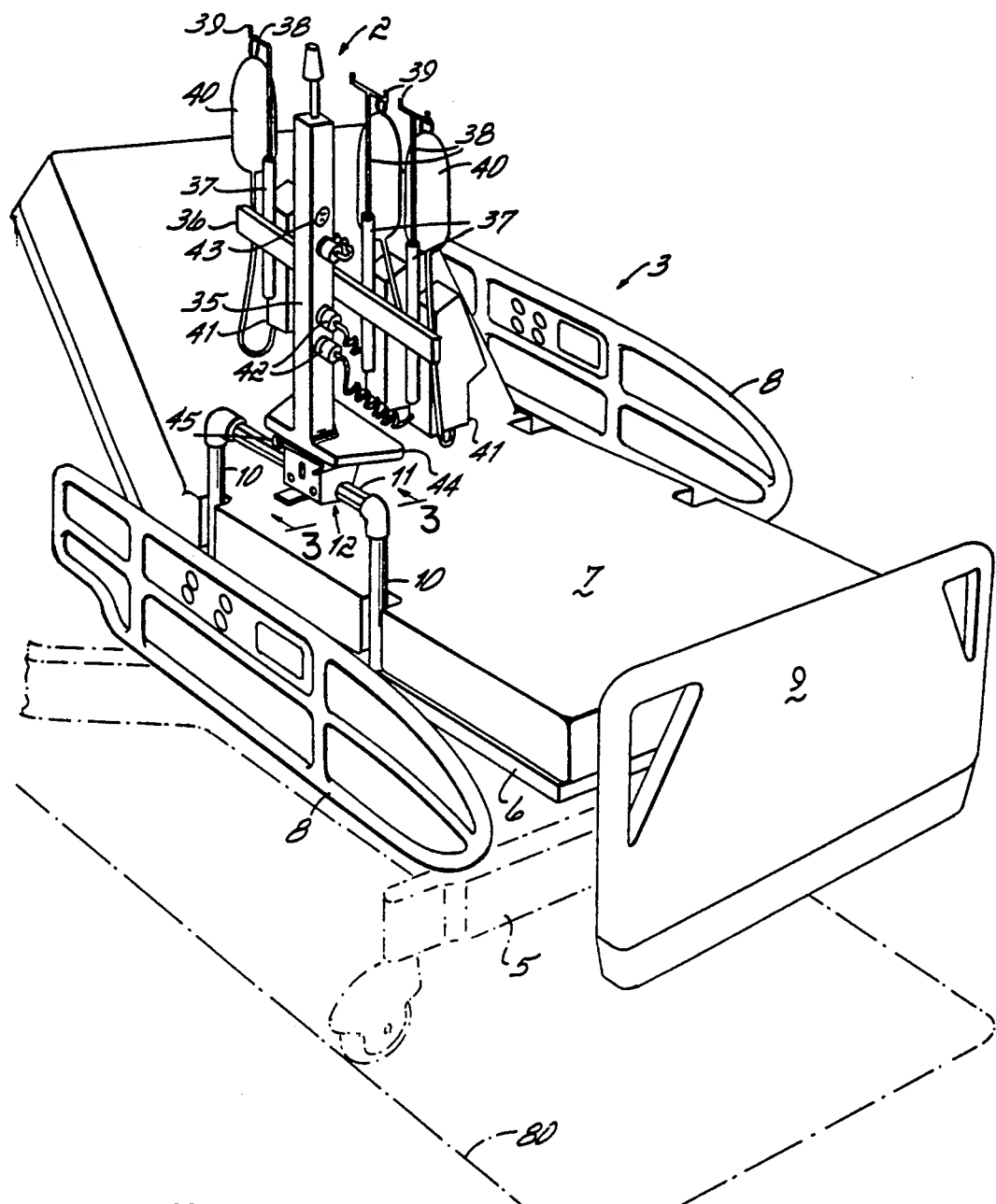
FIG. 2 is a perspective view of the IV rack secured to the bed and located within the footprint of the bed.

Referring now to FIG. 2, it will be seen that IV rack 2, when mounted on the IV rail mounting block 12, falls completely within the footprint 80 of hospital bed 3 defined by projecting downwardly onto a floor surface the periphery of the bed 3. Such a compact configuration greatly facilitates a care provider's maneuvering of bed 3 with IV rack 2 thereon, as the IV rack 2 does not protrude from or otherwise destroy the integrity of the bed footprint. As care providers are adept at maneuvering the bed 3 down aisles, around corners, through doors and the like, the present invention does not require a care provider to in any way alter or otherwise depart from his or her learned bed maneuvering habits.

Should a care provider wish to utilize the IV stand 1 alone, that is, not in conjunction with the IV rack 2 of the present invention, the telescoping rod 27 with hooks 28 thereon (FIG. 1) facilitates such usage.

Those skilled on the art readily recognize numerous adaptations and modifications which can be made to the present invention which will result in an improved IV rack, IV stand and hospital bed, yet all of which will fall within the spirit and scope of the present invention as defined by the following claims. Accordingly, the invention is to be limited only by the following claims and their equivalents.

What is claimed is:

1. The combination comprising:
   a wheeled hospital bed,
   a wheeled IV stand,
   an IV rack,
   means removably mounting said rack to said stand, and
   means for removably mounting said rack to said bed upon severing said rack from said stand and transferring said rack to said bed;
   said means removably mounting said rack to said stand and said means for removably mounting said rack to said bed facilitating generally horizontal, slidable transfer of said IV rack from said stand to said bed and from said bed to said stand;
   said bed defining a footprint on a floor by projecting downwardly thereon a periphery of said bed, said rack being positioned within said bed footprint when said rack is mounted to said bed.

2. The combination comprising:
   a wheeled hospital bed,
   a wheeled IV stand,
   an IV rack,
   means removably mounting said rack to said stand, and
   means for removably mounting said rack to said bed upon severing said rack from said stand and transferring said rack to said bed;
   said bed defining a footprint on a floor by projecting downwardly thereon a periphery of said bed, said rack being positioned within said bed footprint when said rack is mounted to said bed;
   said means removably mounting said rack to said stand comprising:
   a mounting block secured to said stand, and
   means on said rack for slidable engagement with and removable securement to said block.

3. The combination of claim 2 wherein said means on said rack for slidable engagement with and removable securement to said block comprises a downturned channel section bracket having inwardly turned flanges, said flanges being operable to slidably engage a pair of lips on opposed sides of said block.

4. The combination comprising:
   a wheeled hospital bed,
   a wheeled IV stand,
   an IV rack,
   means removably mounting said rack to said stand, and
   means for removably mounting said rack to said bed upon severing said rack from said stand and transferring said rack to said bed;
   said bed defining a footprint on a floor by projecting downwardly thereon a periphery of said bed, said rack being positioned within said bed footprint when said rack is mounted to said bed;
   said means for removably mounting said rack to said bed comprising:
   an IV rail having a pair of vertical posts secured to said bed and a horizontal rail connected between said posts,
   a mounting block mounted on said horizontal rail and adapted for slidable movement along said rail, and
   means on said rack for slidable engagement with and removable securement to said block.

5. The combination of claim 4 wherein said means on said rack for slidable engagement with and removable securement to said block comprises a downturned channel section bracket having inwardly turned flanges, said flanges being operable to slidably engage a pair of lips on opposed sides of said block.

6. A universal IV stand comprising:
   a wheeled base,
   a first vertical pole originating at said base, extending upwardly and terminating in a platform, said platform including means thereon for slidable engagement and removable securement by a severable IV rack,
   a second vertical pole originating at said platform and extending upwardly, and
   a rod slidable upwardly and downwardly into and out of said second vertical pole and having a plurality of hooks at an upper end thereof for supporting a plurality of bags of IV solution;
   whereby said stand may be utilized in conjunction with a severable IV rack adapted to be connected to said engagement and securement means, and may be utilized without the severable rack as a traditional IV stand whereupon bags of IV solution are supported from said hooks.

7. The universal IV stand of claim 6 wherein said slidable engagement and removable securement means comprises a mounting block having a pair of lips on opposed sides thereof, said lips being adapted to be slidably engaged by a downturned channel section bracket having inwardly turned flanges mounted to said IV rack.

8. An IV rack adapted for use with a wheeled IV stand comprising:
   a vertical spine,
   a horizontally oriented arm connected to said spine, and
   a plurality of individual IV poles connected to said horizontal arm;
   said arm and poles adapted to support a plurality of IV bags and infusion pumps,
   said spine including on a lower end thereof means for slidable engagement and removable securement of said IV rack to an IV stand.

9. The IV rack of claim 8 wherein said slidable engagement and removable securement means comprises a downturned channel section bracket having inwardly turned flanges adapted to slidably engage a pair of lips on opposed sides of a mounting block on the IV stand.

10. A hospital bed adapted for use with a removably securable IV rack comprising:
    a wheeled bed support structure,
    a bed frame connected to said support structure,
    an IV rail connected to said bed frame, and
    a mounting block mounted for slidable movement along said rail, said block including means for generally horizontal slidable engagement and removable securement by an IV rack;
    whereby said mounting block facilitates generally horizontal, slidable transfer of the IV rack from an IV stand to said bed and from said bed to the stand.

11. A hospital bed adapted for use with a removably securable IV rack comprising:
    a wheeled bed support structure,
    a bed frame connected to said support structure,
    an IV rail connected to said bed frame, and a mounting block mounted for slidable movement along said rail, said block including means for slidable engagement and removable securement by an IV rack;

said slidable engagement and removable securement means comprising a pair of lips on opposed sides of said block which are operable to be engaged by a downturned channel section bracket having inwardly turned flanges on the IV rack.

12. The hospital bed of claim 11 wherein said rail includes a horizontal section having a hexagonal cross-section, and said block includes a hexagonal bore therethrough for slidable mating engagement with said horizontal section of said rail.

13. The hospital bed of claim 11 wherein said bed defines a footprint on a floor by projecting downwardly thereon a periphery of said bed, and wherein the IV rack and any IV solution bags and pumps mounted thereto are positioned within said bed footprint, when the rack is mounted to said bed.

14. The combination comprising:
a wheeled hospital bed,
a wheeled IV stand,
an IV rack,
means removably mounting said rack to said stand, and
means for removably mounting said rack to said bed upon severing said rack from said stand and transferring said rack to said bed;
said means removably mounting said rack to said stand and said means for removably mounting said rack to said bed facilitating generally horizontal, slidable transfer of said IV rack from said stand to said bed and from said bed to said stand.

* * * * *